US012599547B2

(12) United States Patent
Baratto

(10) Patent No.: US 12,599,547 B2
(45) Date of Patent: Apr. 14, 2026

(54) TOPICAL COMPOSITIONS OPTIMISED FOR EPIDERMAL LIPIDS AND PHOSPHATIDYL GYCEROL

(71) Applicant: Unifarco S.p.A., Santa Giustina (IT)

(72) Inventor: Giovanni Baratto, Santa Giustina (IT)

(73) Assignee: Unifarco S.p.A., Santa Giustina (IT)

( * ) Notice: Subject to any disclaimer, the term of this patent is extended or adjusted under 35 U.S.C. 154(b) by 417 days.

(21) Appl. No.: 18/546,279

(22) PCT Filed: Feb. 15, 2022

(86) PCT No.: PCT/IB2022/051330

§ 371 (c)(1),
(2) Date: Aug. 14, 2023

(87) PCT Pub. No.: WO2022/175811

PCT Pub. Date: Aug. 25, 2022

(65) Prior Publication Data

US 2024/0130941 A1 Apr. 25, 2024

(30) Foreign Application Priority Data

Feb. 16, 2021 (IT) ........................ 102021000003539

(51) Int. Cl.

| | |
|---|---|
| ***A61K 8/42*** | (2006.01) |
| ***A61K 8/06*** | (2006.01) |
| ***A61K 8/36*** | (2006.01) |
| ***A61K 8/63*** | (2006.01) |
| ***A61Q 19/08*** | (2006.01) |

(52) U.S. Cl.
CPC ................ *A61K 8/42* (2013.01); *A61K 8/064* (2013.01); *A61K 8/361* (2013.01); *A61K 8/63* (2013.01); *A61Q 19/08* (2013.01)

(58) Field of Classification Search
None
See application file for complete search history.

(56) References Cited

FOREIGN PATENT DOCUMENTS

| | | | |
|---|---|---|---|
| EP | 3125865 | B1 | 5/2019 |
| JP | 2006199633 | A | 8/2006 |
| KR | 20100026143 | A | 3/2010 |
| KR | 20130119587 | A | 11/2013 |
| WO | 2010010985 | A1 | 1/2010 |

OTHER PUBLICATIONS

Search Report and Written Opinion of PCT/IB2022/051330 issued Apr. 21, 2022.

*Primary Examiner* — Samantha L Shterengarts
(74) *Attorney, Agent, or Firm* — Silvia Salvadori, P.C.; Silvia Salvadori

(57) ABSTRACT

Topical composition comprising as an active agent an association comprising: a) at least one ceramide, b) at least one saturated fatty acid C12-C22; c) cholesterol, said topical composition comprising phosphatidyl glycerol; wherein: said components a), b) c) and phosphatidyl glycerol are dispersed as such within said topical composition and phosphatidylglycerol is present in a weight ratio with respect to said ceramide comprised between 1:4 and 2:4.

15 Claims, 4 Drawing Sheets

—◆—Cream 1 (Day 6) G' 23-55°C          ◇ Cream 1 (Day 6) G' 55-23°C

—▲—Cream 1 (Day 6) G" 23-55°C          △ Cream 1 (Day 6) G" 55-23°C

—■—Cream 2 (Day 5) G' 23-55°C          □ Cream 2 (Day 5) G' 55-23°C

—●—Cream 2 (Day 5) G" 23-55°C          ○ Cream 2 (Day 5) G" 55-23°C

TOPICAL COMPOSITIONS OPTIMISED FOR EPIDERMAL LIPIDS AND PHOSPHATIDYL GYCEROL

This application is a U.S. national stage of PCT/IB2022/051330 filed 15 Feb. 2022, which claims priority to, and the benefit of Italian Application No. 102021000003539 filed on 16 Feb. 2021, the contents of which are incorporated herein by reference in their entireties.

FIELD OF THE INVENTION

The present invention relates to topical compositions based on epidermal lipids and phosphatidyl glycerol suitably mixed to obtain stable and effective formulations.

PRIOR ART

Most of the technical problems related to the formulation of a cosmetic product can be overcome through a careful choice of raw materials, but it is impossible to predict the interaction between the functional active ingredients and the ingredients (emulsifiers, polymers, oils) that make up the vehicle. It should be noted that the vehicle itself contributes to the effectiveness of the product and not only the use of active ingredients in high concentration. The first efficacy and safety requirement is therefore only met if stability of the product can be ensured over time.

The first part of the formulation process coincides with the widest and most detailed possible definition of the desired functions in the finished product. In practice it is necessary to list a set of properties that the product must possess in order to identify the most suitable ingredients.

It follows that the choice of raw materials will affect many other variables of the final formula, such as stability, sensory characteristics, skin tolerability and costs, to list a few.

For a correct formulation it is essential to know other parameters such as the packaging in which the product will be sold and, last but not least, the physiology of the skin area on which the product is to be applied; thus, the biochemistry of the active ingredients and the transdermal passage, as well as the state of the skin (and the presence of any pathological dysfunctions) must also be evaluated, as must age.

There are numerous emollient/moisturising or protective topical formulations available on the market and, in most cases, when applied to the skin affected by skin diseases, they perform their emollient activity by creating a relatively waterproof layer on the skin surface on which they are applied. This results in a more or less occlusive effect comparable to that exerted by a plastic film applied on the same skin surface to be protected and treated.

The layer of cream, which is difficult for the skin to absorb, is easily removed using ordinary detergents as well as by involuntary mechanical action.

An improvement over such formulations is given by the topical formulations described in patent IT 1363475 on behalf of the Applicant, having barrier repair as an action.

In a formulation for topical use, barrier repairers are those emollients which, in addition to lipids normally used, also contain specific agents capable of stimulating the endogenous synthesis of lipids that constitute the intercellular cement of the stratum corneum (ceramides, cholesterol, fatty acids).

It is known that atopic dermatitis is a disease characterised by an increased barrier permeability that depends mainly on a deficiency of ceramides. The topical application of small amounts of the mixture of epidermal lipids that constitutes the cement of the stratum corneum (adequate ratio of ceramides, cholesterol and fatty acids) produces significant effects on barrier restructuring and indirectly acts on the inflammatory state induced by damage to the barrier.

The literature shows that, in the stratum corneum, epidermal lipids consist mainly of an equimolar mixture of ceramides (45-50%), cholesterol (20-25%) and free fatty acids (10-15%). In addition, there is a much lower amount of cholesterol sulfate (2-5%) and non-polar lipids. Ceramides consist of a variable-chain fatty acid linked to a sphingosine, which is also variable-chain. To date, 18 subclasses of ceramides have been identified [Motta S et al. *Biochim Biophys Acta, Mol Basis Dis* 1993, 1182, 147-51], each possessing chains of variable length and functional groups, as described in the FIG. 1 taken from J. van Smeden et al./*Biochimica et Biophysica Acta* 1841 (2014) 295-313.

The optimised mixtures of epidermal lipids that respect physiological relationships are now considered by the scientific literature to be the most effective active ingredients in the management of skin alterations characterised by damage to the barrier, such as atopic dermatitis. In the Italian patent IT 1363475, the Applicant has disclosed a formulation for topical use characterised by an exact 3:1:1 ratio of the three fundamental lipids.

In addition, a correct epidermal barrier is also linked to correct hydration; hence the ability to maintain a proper physiological skin condition is also sought in anti-ageing products.

Several studies have demonstrated that ceramides play an essential role in both the barrier and the water retention function of the healthy stratum corneum, suggesting that stratum corneum dysfunction resulting from ceramide deficiency is associated with ageing. Further studies show that as a result of ageing there is a different distribution of epidermal lipids compared to the 3:1:1 described above. In particular, there is a defect in the synthesis of cholesterol, demonstrating that equimolar mixtures of the three fundamental lipids or, even better, mixtures with a predominance of cholesterol are very useful in restoring a correct skin barrier in skin subject to ageing. [Peter M. Elias, Kenneth R. Feingold, *Skin Barrier*, Ed. Taylor & amp; Francis Group LLC, 2006; pp. 535-52].

Formulations containing ceramides present the problem of solubilisation of this raw material in the final formulation, requiring careful and continuous control in the production phases of industrial scale-up.

To overcome the problem, it is possible to act on the production method, varying the order of the stages of addition of raw materials; however, the heating process at high temperatures, normally necessary to dissolve waxes, for example, could cause the degradation of other raw materials that make up the formula. A good compromise may be the pre-solution with a solvent.

However, the selection of the right solvent that leads to the formulation of a product for safe, stable and effective topical use requires careful evaluation, on the part of the formulator, of several factors:

- solvent behaviour in the base (vehicle);
- tolerability after application (also linked to the peculiar characteristics of the application site). (For example, tissue inflamed by dermatitis);
- compliance by the end user. (The formulated product should be pleasant and used several times).

WO2010/010985 and KR2010/010985 disclose topical compositions based on ceramide in which ceramide and optional components like saturated fatty acid esters are contained in a multilayer lamellar coating of granules, which are thereafter dispersed within said topical compositions.

KR2013/0119587 disclose a process for preparing multilamellar liquid crystals fo solubilizing an insoluble substance (for example ceramide) containing the following components a) a phospholipid, b) a neutral fat, c) a polyol, d) cholesterol.

SUMMARY OF THE INVENTION

The Applicant has now surprisingly discovered that phosphatidyl glycerol, added in appropriate proportions to a formulation comprising ceramides, manages to solubilise the ceramides completely and thus contributes to creating a composition for stable topical use over time.

In addition, phosphatidyl glycerol has numerous other functions that make it an optimal solvent to satisfy all the features described above.

The subject matter of the present invention is therefore topic compositions comprising as an active agent an association comprising:

a) at least one ceramide, b) at least one saturated fatty acid $C_{12}$-$C_{22}$;

c) cholesterol, said topical composition comprising phosphatidylglycerol wherein said components a), b) and c) and phosphatidylglycerol are dispersed as such within said topical composition;

phosphatidylglycerol is present weight ratio with respect to said ceramide comprised between 1:4 and 2:4.

DETAILED DESCRIPTION OF THE INVENTION

For the purposes of the present invention, the definitions "comprising" and "containing" provide for the possibility of further components in addition to those mentioned after said definition.

Conversely, for the purposes of the present invention the definition "consisting of" excludes the possibility of further components other than those listed after said definition.

For the purposes of the present invention with the wording "said components a), b) and c) and phosphatidylglycerol are dispersed as such within said topical composition" it is meant to exclude from that the aforementioned components are previously incorporated in micro-vehicular system like those mentioned in WO2010/010985, KR2010/010985 and KR2013/0119587, before being dispersed in a final topical composition.

For the purposes of the present invention, phosphatidyl glycerol means a compound characterised by the following formula:

(I)

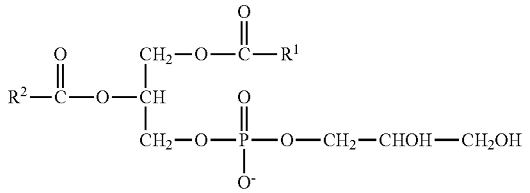

wherein R1 and R2 are linear or branched $C_{12}$-$C_{20}$ alkyl residues, the same or different from each other and possibly containing one or more ethylenic unsaturations, preferably are $C_{14}$-$C_{20}$ more preferably are $R1=R2=C_{17}$ and among them the most preferred phosphatidyl glycerol 1,2, dilinoleoyl-phosphatidyl glycerol, $R1=C_{15}$, $R2=C_{19}$ and among them the most preferred phosphatidyl glycerol is 1-palmitoyl, 2-arachidonyl-phosphatidyl glycerol; $R1=C_{15}$, $R2=C_{17}$ and among them the most preferred phosphatidyl glycerol is 1-palmitoyl, 2-lynoleoyl-phosphatidyl glycerol.

Figure 1:
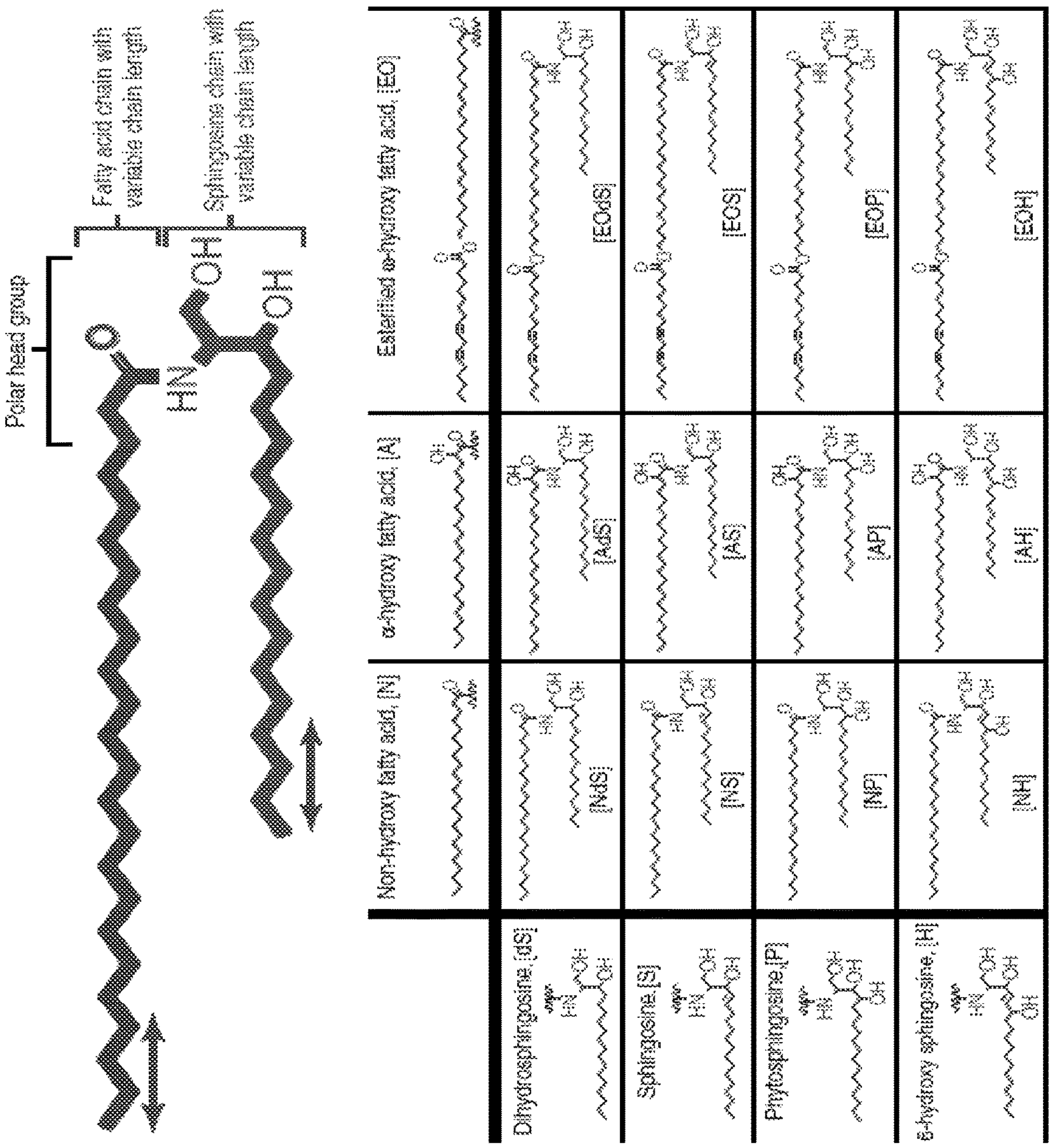
FIG. 1 shows the chemical formulas of some of the ceramides that may be used in the composition according to the present invention.

In the composition according to the present invention, any type of ceramide or component a) of those indicated in FIG. 1 may be used as a ceramide, although particularly preferred are, for example, N-acetlylsphingosine (ceramide 2 or NS) or phytosphingosine amide with stearic acid (ceramide 3 or NP). Phytosphingosine amide with stearic acid is preferably used.

Preferably ceramide is added to the topical composition is admixture with phospahtodylglycerol.

Phosphatidyl glycerol is preferably present in the topical composition according to the present invention in a weight ratio of phosphatidyl glycerol/ceramide of 1:3.

In the topical composition that is the subject matter of the present invention the a/b/c ratio is preferably 3:1:1.

In this case it exerts a strong barrier effect on the skin, thus preventing and treating skin damage.

According to another preferred embodiment of the invention, the weight ratio a/b/c is 2:1:1. In this case the topical composition of the invention exerts a lower barrier effect, but can nevertheless be advantageously employed to prevent and treat skin damage.

According to another embodiment of the inventive topical composition, the weight ratio a/b/c is 1:1:1. In this case it is employed to prevent skin imperfections such as wrinkles, skin spots etc. caused by ageing.

Finally, a further embodiment of the topical composition of the invention is that in which the weight ratio a/b/c is 1:2:1 and is used primarily to treat the skin of the elderly.

According to a further embodiment of the invention, the topical composition that is the subject matter of the invention can also contain cholesterol sulfate. In this case it can be used to prevent and treat psoriasis. Cholesterol sulphate is present here as sodium salt.

The topical composition according to the present invention contains each components a), b), c) and the optional component d) in concentrations varying between 0.01 and 5% by weight on the total weight of said composition, preferably between 0.1 and 2% by weight.

The topical composition that is the subject matter of the present invention may be in the form of an oil-in-water emulsion in which case it is substantially hydrophilic, or may also actually be an water in oil emulsion and thus be substantially lipophilic.

Example 1 Microscopic Comparison of the Formulation According to the Present Invention with Standard Formulation The following formulations were used:

Cream 1 standard composition (a/b/c ratio of 3:1:1) without phosphatidyl glycerol and disclosed in IT 1363475, that was subjected to Cream 2 composition according to the present invention (a/b/c ratio of 3:1:1) also containing phosphatidyl glycerol, wherein the phosphatidyl glycerol/ceramide weight ratio is 1:3.

In particular, the Applicant has gathered evidence to the effect that the formula thus obtained is structurally better.

Microscope images at 40× magnification of the following formulations were compared:

CREAM 1: standard formula 3:1:1, batch of 4 kg

CREAM 2: standard formula 3:1:1 with added phosphatidyl glycerol, batch of 4 kg

Figure 2:
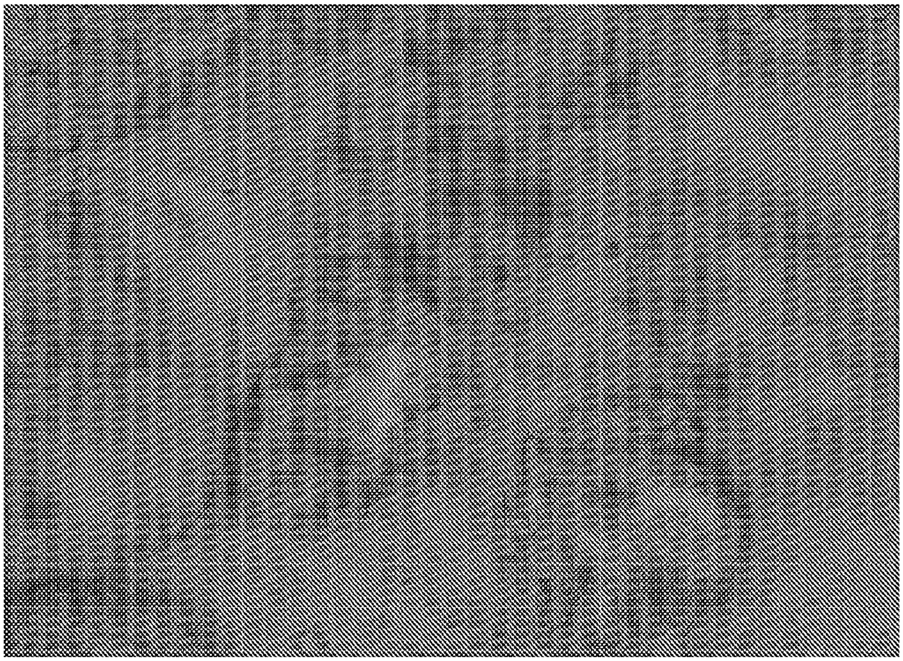
FIG. 2 represents a photo magnified 40× under the SEM Microscope with an enlargement of the formulation of the state of the art with an a/b/c ratio of 3:1:1, disclosed in IT 1363475.
Figure 3:
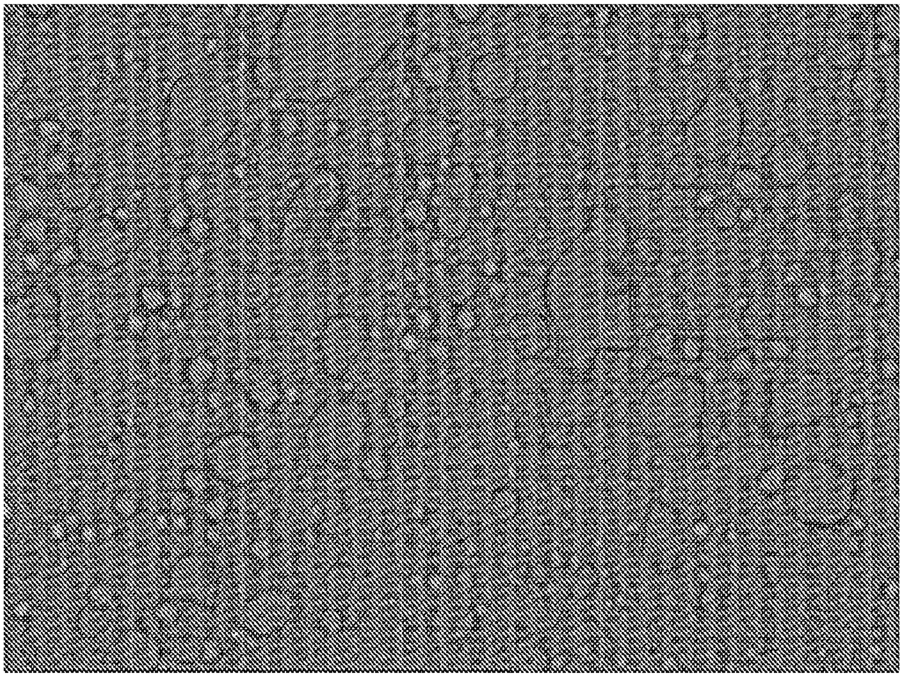
FIG. 3 depicts a photo magnified 40× under the SEM Microscope of the cream with an a/b/c ratio of 3:1:1 and formulated according to the present invention.

The images clearly show the different structure of the formula containing the new ingredient phosphatidyl glycerol. Cream 2, formulated according to the invention, as shown in FIG. 3, is much more homogeneous than cream 1 (FIG. 2): a better dispersion of the dispersed phase in the dispersing phase can be noted.

From the data it can be concluded that:

the inclusion of ceramide in the formula after mixing in phosphatidyl glycerol results in a better mixing of the ceramide in the finished product;

surprisingly, the presence of the new ingredient phosphatidyl glycerol also determines a better structuring of the product itself.

Example 2 Rheological Analysis Comparison of a Formulation According to the Present Invention with a Standard Formulation A rheological analysis was also performed in order to highlight any differences between the product with standard composition (a/b/c ratio of 3:1:1) without phosphatidyl glycerol, disclosed in IT 1363475, and the new formula.

Figure 4:
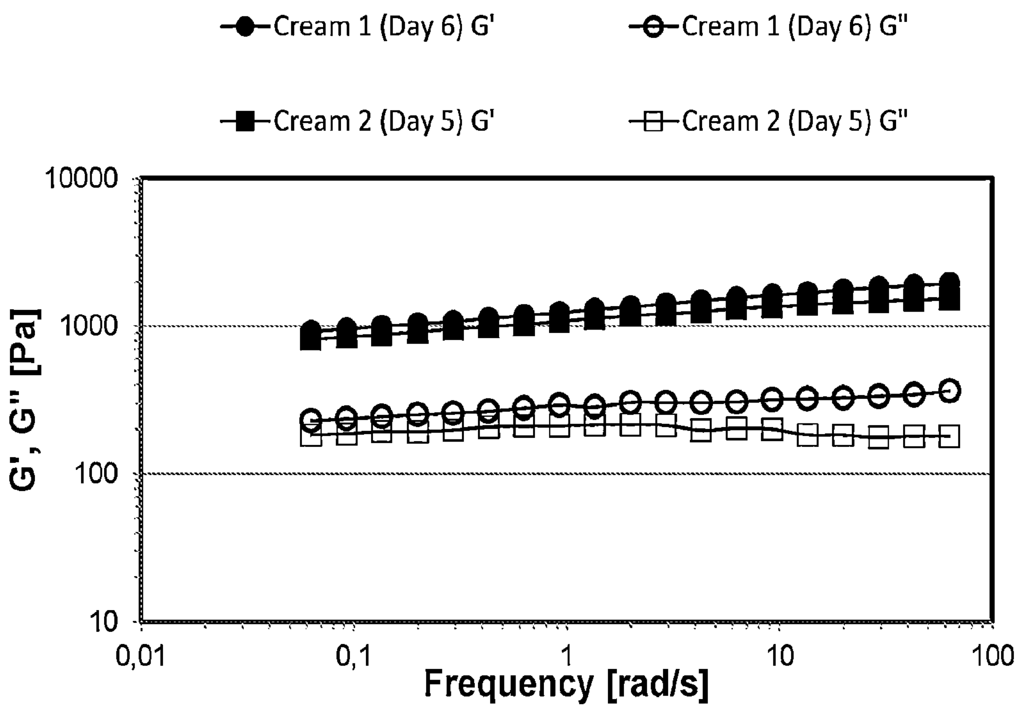
FIG. 4 shows the results of the frequency sweep by evaluating the performance of the elastic modulus G' and the viscous modulus G" as a function of the frequency of the formulation of the state of the art with an a/b/c ratio of 3:1:1, disclosed in IT 1363475, and of the product of the invention.
Figure 5:
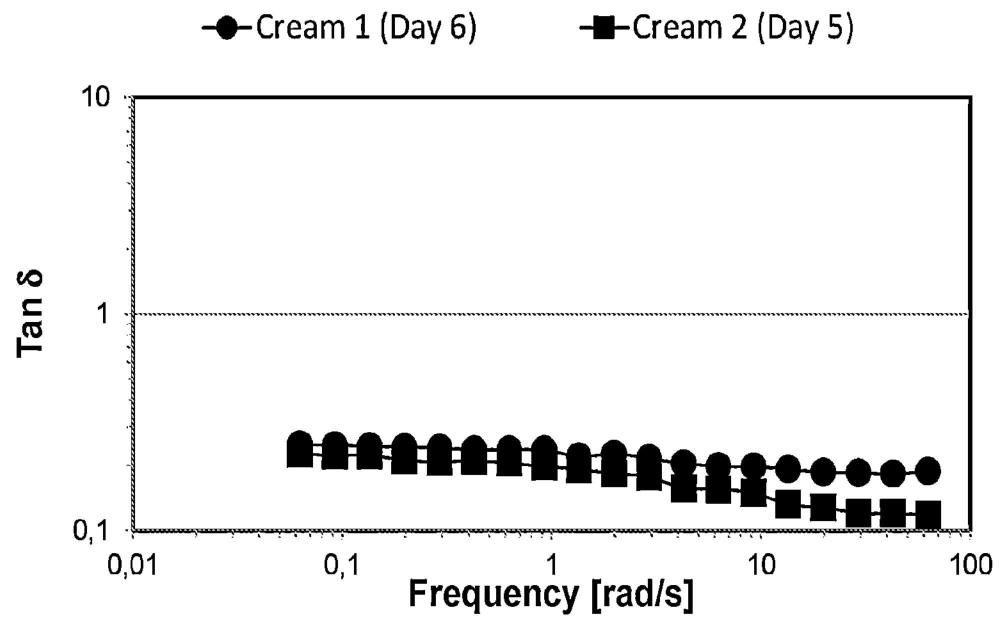
FIG. 5 illustrates the results of the trend of the loss factor tan δ as a function of the frequency of the formulation of the state of the art with an a/b/c ratio of 3:1:1, disclosed in IT 1363475, and of the product of the invention.

1.1. Frequency Sweep and Loss Factor tan δ (FIGS. 4 and 5)

A frequency analysis, performed to highlight possible instability in the short and medium term showed no marked differences between the samples. The qualitative trend of the profiles is the same, while the minimal differences in the values of the modules, which result in minimal differences in the viscosity values, can be linked to the production methods (FIG. 4). The similarity of the graphs in FIG. 4 can also be read through the trend of the loss factor (tan δ) as a function of the oscillation frequency (FIG. 5). In fact, the loss factor is given by the ratio between the viscous component and the elastic one of the material, while the ratio G"/G' remains constant as the oscillation frequency varies.

Figure 6:
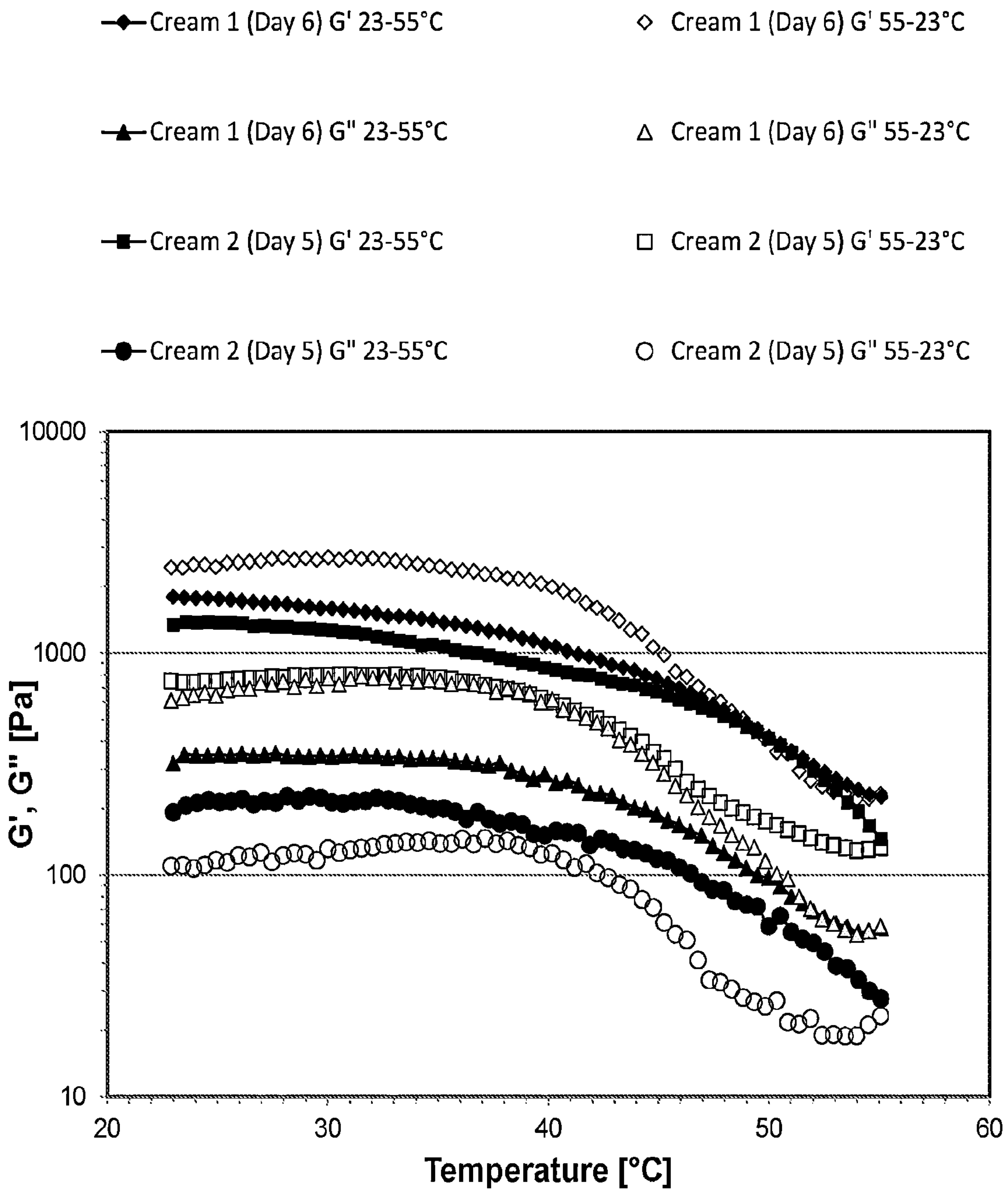
FIG. 6 gives data from the temperature analysis, evaluating the trend of the elastic modulus G' and viscous modulus G" as a function of the temperature from 23 to 55° C. of the formulation of the state of the art with an a/b/c ratio of 3:1:1, disclosed in IT 1363475, and of the product of the invention.

2.2. Temperature Sweep Test (FIG. 6)

The black dots represent the profile obtained in the heating ramp, while the empty ones represent the profile obtained in the cooling ramp.

In the cooling ramp a qualitative difference between the standard sample and the new formula, which reflects a slightly different structure, can be noted. If, in the standard product, the values of the viscoelastic profiles at the end of cooling are higher than the starting ones, the final values of the viscoelastic modules are slightly lower in the case of the new formula. The qualitative difference, however, does not represent an instability of the formula, since the elastic and viscous moduli vary analogously with respect to each other as a function of temperature, maintaining the same distance in the graph.

In conclusion, the comparative rheological analysis showed no differences that could reflect a possible instability in the short and medium term of the new formula and that could adversely affect the processing process.

Examples of preferred formulations include, but are not limited to:

| 1. Water-in-oil emulsion | |
|---|---|
| WATER | 58,714 ÷ 67,011 |
| OILS (Liquid paraffin, Squalane, Isohexadecane etc.) | 12,000 ÷ 36,000 |
| GLYCOLS (Glycerin) | 3,262 ÷ 4,579 |
| BUTTERS AND WAXES (Butyrospermum parkii) | 3,680 ÷ 4,200 |
| EMULSIFIERS (Sorbitan Sterarate, Polyglyceryl-3 polyricinoleate) | 1,840 ÷ 2,100 |
| PRESERVATIVES AND STABILISERS (Pentylene glycol, Magnesium sulfate, Magnesium, Stearate | 5,600-6,500 |
| Ceramides | 0.01 ÷ 5 |
| Phosphatidylglycerol | 0.01 ÷ 5 |
| Cholesterol | 0.01 ÷ 5 |
| Stearic acid | 0.01 ÷ 5 |

| 2. Oil-in-water emulsion | |
|---|---|
| WATER | 56,548 ÷ 64,538 |
| OILS (Hydrogenated polydecene, Squalane) | 7,360 ÷ 13,400 |
| BUTTERS AND WAXES (Butyrospermum parkii) | 3,680 ÷ 4,200 |
| GLYCOLS (Glycerin, Caprylyl glycol) | 3,662 ÷ 4,179 |
| EMULSIFIERS (Tribehenin PEG-20 esters, PEG-100 stearate, Lecithin) | 1,000 ÷ 4,000 |
| PRESERVATIVES AND STABILISERS (Polysorbate 60, o-Cimen-5-ol) | 5,600 ÷ 6,500 |
| POLYMERS (Ammonium acryloyldimethyltaurate/VP copolymer (vinyl pyrrolidone), Hydroxyethyl acrylate/Sodium acryloyldimethyl taurate copolymer, Xanthan gum) | 1,360 ÷ 2,400 |
| Ceramides | 0.01 ÷ 5 |
| Phosphatidylglycerol | 0.01 ÷ 5 |
| Cholesterol | 0.01 ÷ 5 |
| Stearic acid | 0.01 ÷ 5 |

| 3. Detergent | |
|---|---|
| WATER | 56,548 ÷ 64,538 |
| OILS (Dimethicone, Dimethicone Crosspolymer, Isohexadecane, Squalane) | 7,360 ÷ 13,400 |
| BUTTERS AND WAXES (Butyrospermum parkii) | 3,680 ÷ 4,200 |
| GLYCOLS (Glycerin, Caprylyl glycol) | 3,662 ÷ 4,179 |
| PRESERVATIVES AND STABILISERS (Polysorbate 80, Tocopheryl Acetate, Arginine, Lauryl Glucoside, Capryloyl Glycine, Caprylyl Glycol) | 5,600 ÷ 6,500 |

-continued

| 3. Detergent | |
|---|---|
| POLYMERS (Ammonium acryloyldimethyltaurate/VP copolymer (vinyl pyrrolidone), Copolymer Hydroxyethyl acrylate/Sodium acryloyldimethyl taurate, Dehydroxanthan gum, Sodiom hyaluronate) | 2,468 ÷ 3,237 |
| Ceramides | 0.01 ÷ 5 |
| Phosphatidyl glycerol | 0.01 ÷ 5 |
| Cholesterol | 0.01 ÷ 5 |
| Stearic acid | 0.01 ÷ 5 |

| 4. Lipstick | |
|---|---|
| OILS (Octyldodecanol, Hydrogenated polydecene) | 12,000 ÷ 36.00 |
| BUTTERS AND WAXES (Butyrospermum parkii, Glyceryl behenate, Dehydrogenated microcrystalline wax, Synthetic wax, Tribehenin, glyceryl behenate) | 3,680 ÷ 4,200 |
| PRESERVATIVES AND STABILISERS (Pentaerythritol tetrakis) | |
| Ceramides | 0.01 ÷ 5 |
| Phosphatidylglycerol | 0.01 ÷ 5 |
| Cholesterol | 0.01 ÷ 5 |
| Stearic acid | 0.01 ÷ 5 |

The invention claimed is:

1. Topical composition comprising as an active agent an association comprising:

a) at least one ceramide b) at least one saturated fatty acid $C_{12}$-$C_{22}$;

c) cholesterol, said topical composition comprising phosphatidylglycerol wherein:

said components a), b) and c) and phosphatidylglycerol are dispersed as such within said topical composition;

the phospatidylglycerol is present in a weight ratio with respect to said ceramide comprised between 1:4 and 2:4.

2. Topical composition according to claim 1, wherein ceramide is added to said topical composition in admixture with phoshatidylglycerol.

3. Topical composition according to claim 1, wherein said phosphatidylglycerol/ceramide weight ratio is 1:3.

4. Topical composition according to claim 1, wherein the phosphatidyl glycerol has the following formula:

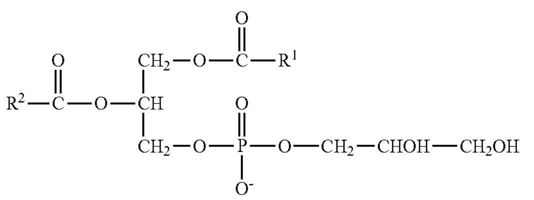

wherein R1 and R2 are linear or branched $C_{12}$-$C_{20}$ alkyl residues, equal or different from each other and optionally containing one or more ethylenic unsaturation.

5. Topical composition according to claim 1 wherein said ceramide or component a) is selected from N-acetylfingosine (ceramide 2 or NS) or the amide of phytosphingosine with stearic acid (Ceramide 3 or NP).

6. Topical composition according to claim 1, wherein said saturated fatty acid b) is a $C_{16}$-$C_{18}$ fatty acid.

7. Topical composition according to claim 1, comprising a fourth component d) consisting of cholesterol sulphate.

8. Topical composition according to claim 7, wherein said cholesterol sulphate is in the form of sodium salt.

9. Topical composition according to claim 1, containing each component a), b), c) and any component d) in concentrations between 0.01 and 5% by weight on the total weight of said composition.

10. Topical composition according to claim 1 in the form of an oil-in-water emulsion.

11. Topical composition according to claim 10, wherein said oil-in-water emulsion is in the form of a substantially hydrophilic emulsion.

12. Topical composition according to claim 1 in the form of a water-in-oil emulsion.

13. Topical composition according to claim 12, wherein said water-in-oil emulsion is a substantially lipophilic emulsion.

14. A method for treating damage to the skin barrier layer comprising administering to a subject in need thereof a topical composition comprising as an active agent an association comprising:

a) at least one ceramide;

b) at least one saturated fatty acid $C_{12}$-$C_{22}$; and c) cholesterol;

said topical composition comprising phosphatidylglycerol, wherein:

said components a), b) and c) and phosphatidylglycerol are dispersed as such within said topical composition;

the phospatidylglycerol is present in a weight ratio with respect to said ceramide comprised between 1:4 and 2:4, weight ratios of the a/b/c components selected from 3:1:1, and 2:1:1.

15. A method for treating skin of elderly subjects comprising administering to said subjects a topical composition comprising as an active agent an association comprising:

a) at least one ceramide;

b) at least one saturated $C_{12}$-$C_{22}$fatty acid; and c) cholesterol, said topical composition comprising phosphatidylglycerol, wherein:

said components a), b) and c) and phosphatidylglycerol are dispersed as such within said topical composition;

the phosphatidylglycerol is present in a weight ratio with respect to said ceramide comprised between 1:4 and 2:4, weight ratios a/b/c is 1:2:1.

* * * * *